United States Patent
O'Grady et al.

(10) Patent No.: US 11,946,037 B2
(45) Date of Patent: Apr. 2, 2024

(54) METHOD FOR DIGESTING NUCLEIC ACID IN A SAMPLE

(71) Applicant: UEA Enterprises Limited, Norwich (GB)

(72) Inventors: Justin Joseph O'Grady, Norwich (GB); Gemma Louise Kay, Norwich (GB); Themoula Charalampous, Norwich (GB); Alp Aydin, Norwich (GB); Riccardo Scotti, Norwich (GB)

(73) Assignee: UEA Enterprises Limited, Norwich (GB)

( * ) Notice: Subject to any disclaimer, the term of this patent is extended or adjusted under 35 U.S.C. 154(b) by 0 days.

(21) Appl. No.: 17/779,414

(22) PCT Filed: Nov. 24, 2020

(86) PCT No.: PCT/GB2020/052986
§ 371 (c)(1),
(2) Date: May 24, 2022

(87) PCT Pub. No.: WO2021/105659
PCT Pub. Date: Jun. 3, 2021

(65) Prior Publication Data
US 2023/0203472 A1 Jun. 29, 2023

(30) Foreign Application Priority Data
Nov. 25, 2019 (GB) ...................................... 1917101

(51) Int. Cl.
*C12N 15/10* (2006.01)
*C12N 9/22* (2006.01)
(52) U.S. Cl.
CPC ........... *C12N 15/1003* (2013.01); *C12N 9/22* (2013.01)
(58) Field of Classification Search
CPC .............................. C12N 15/1003; C12N 9/22
USPC ....................................................... 536/25.4
See application file for complete search history.

(56) References Cited

U.S. PATENT DOCUMENTS 5,470,711 A 11/1995 Bean et al.

FOREIGN PATENT DOCUMENTS

| CN | 107227211 A | 10/2017 |
| WO | 2007071442 A2 | 6/2007 |
| WO | 2008013838 A2 | 1/2008 |
| WO | 2009097567 A1 | 8/2009 |
| WO | 2016169579 A1 | 10/2016 |
| WO | 2017118719 A1 | 7/2017 |

OTHER PUBLICATIONS

PubChem SID 87575650, Deposit: Mar. 2, 2010 (pp. 1-6) and PubChem CID 198016, Create: Aug. 9, 2005 (pp. 7-29) (Year: 2010).*
Ayusa-Sacido, A. et al.; "Activated EGFR signaling increases proliferation, survival, and migration and blocks neuronal differentiation in post-natal neural stem cells"; Journal of Neuro-Oncology, vol. 97, Issue No. 3; 2010; pp. 323-337.
Charalampous, T. et al.; "Rapid Diagnosis of Lower Respiratory Infection using Nanopore-based Clinical Metagenomics"; bioRxiv preprint; 2018; 40 pages; doi: https://doi.org/10.1101/387548.
Faria, MMP. et al.; "The development and application of a molecular community profiling strategy to identify polymicrobial bacterial DNA in the whole blood of septic patients"; BMC Microbiology, vol. 15, Issue No. 1; 2015; 16 pages; DOI: 10.1186/s12866-015-0557-7.
GB1917101.6 Search Report Under Section 17 and 18(3); date of search: May 26, 2020; 5 pages.
International Search Report and Written Opinion for International Application PCT/GB2020/052986; International Filing Date: Nov. 24, 2020; dated Feb. 24, 2021; 12 pages.
Wanidworanun, C. et al.; "Antisense oligonucleotides targeting malarial aldolase inhibit the asexual erythrocytic stages of Plasmodium falciparum"; Molecular and Biochemical Parasitology, vol. 102, Issue No. 1; 1999; pp. 91-101.

* cited by examiner

*Primary Examiner* — Yih-Horng Shiao
(74) *Attorney, Agent, or Firm* — Karen A. LeCuyer; DeWitt LLP

(57) ABSTRACT

Provided are methods, compositions and kits for depleting host nucleic acid in a biological sample, said sample having been previously obtained from an animal host.

13 Claims, No Drawings

Specification includes a Sequence Listing.

SEQUENCE LISTING

<160> NUMBER OF SEQ ID NOS: 2

<210> SEQ ID NO 1
<211> LENGTH: 213
<212> TYPE: PRT
<213> ORGANISM: Artificial Sequence
<220> FEATURE:
<223> OTHER INFORMATION: HL-SAN DNase

<400> SEQUENCE: 1

```
Ala Pro Pro Ser Ser Phe Ser Lys Ala Lys Lys Glu Ala Val Lys Ile
1               5                   10                  15

Tyr Leu Asp Tyr Pro Thr Glu Phe Tyr Cys Gly Cys Asp Ile Thr Trp
                20                  25                  30

Lys Asn Lys Lys Lys Gly Ile Pro Glu Leu Glu Ser Cys Gly Tyr Gln
            35                  40                  45

Val Arg Lys Gln Glu Lys Arg Ala Ser Arg Ile Glu Trp Glu His Val
    50                  55                  60

Val Pro Ala Trp Gln Phe Gly His Gln Arg Gln Cys Trp Gln Lys Gly
65                  70                  75                  80

Gly Arg Lys Asn Cys Thr Arg Asn Asp Lys Gln Phe Lys Ser Met Glu
                85                  90                  95

Ala Asp Leu His Asn Leu Val Pro Ala Ile Gly Glu Val Asn Gly Asp
                100                 105                 110

Arg Ser Asn Phe Arg Phe Ser Gln Trp Asn Gly Ser Lys Gly Ala Phe
            115                 120                 125

Tyr Gly Gln Cys Ala Phe Lys Val Asp Phe Lys Gly Arg Val Ala Glu
    130                 135                 140

Pro Pro Ala Gln Ser Arg Gly Ala Ile Ala Arg Thr Tyr Leu Tyr Met
145                 150                 155                 160

Asn Asn Glu Tyr Lys Phe Asn Leu Ser Lys Ala Gln Arg Gln Leu Met
                165                 170                 175

Glu Ala Trp Asn Lys Gln Tyr Pro Val Ser Thr Trp Glu Cys Thr Arg
                180                 185                 190

Asp Glu Arg Ile Ala Lys Ile Gln Gly Asn His Asn Gln Phe Val Tyr
            195                 200                 205

Lys Ala Cys Thr Lys
    210
```

<210> SEQ ID NO 2
<211> LENGTH: 209
<212> TYPE: PRT
<213> ORGANISM: Artificial Sequence
<220> FEATURE:
<223> OTHER INFORMATION: M-SAN DNase

<400> SEQUENCE: 2

```
Ala Pro Ile Ser Phe Ser His Lys Asn Glu Ala Val Lys Ile Tyr
1               5                   10                  15

Arg Asp His Pro Val Glu Phe Tyr Cys Gly Cys Glu Ile Arg Trp Gln
                20                  25                  30

Gly Lys Lys Gly Ile Pro Asp Leu Glu Ser Cys Gly Tyr Gln Val Arg
            35                  40                  45

Lys Asn Glu Asn Arg Ala Ser Arg Ile Glu Trp Glu His Val Val Pro
    50                  55                  60

Ala Trp Gln Phe Gly His Gln Leu Gln Cys Trp Gln Gln Gly Gly Arg
65                  70                  75                  80
```

-continued

```
Lys Asn Cys Thr Arg Thr Ser Pro Glu Phe Asn Gln Met Glu Ala Asp
                85                  90                  95

Leu His Asn Leu Val Pro Ala Ile Gly Glu Val Asn Gly Asp Arg Ser
            100                 105                 110

Asn Phe Arg Phe Ser Gln Trp Asn Ser Lys Gly Ala Phe Tyr Gly Gln
        115                 120                 125

Cys Ala Phe Lys Val Asp Phe Lys Gly Arg Val Ala Glu Pro Pro Ala
    130                 135                 140

Gln Ser Arg Gly Ala Ile Ala Arg Thr Tyr Leu Tyr Met Ser Glu Gln
145                 150                 155                 160

Tyr Gly Leu Arg Leu Ser Lys Ala Gln Asn Gln Leu Met Gln Ala Trp
            165                 170                 175

Asn Asn Gln Tyr Pro Val Ser Glu Trp Glu Cys Val Arg Asp Gln Lys
            180                 185                 190

Ile Glu Lys Val Gln Asn Ser Asn Arg Phe Val Arg Glu Gln Cys Pro
        195                 200                 205

Asn
```

METHOD FOR DIGESTING NUCLEIC ACID IN A SAMPLE

CROSS REFERENCE TO RELATED APPLICATIONS

This application is a National Stage application of PCT/GB2020/052986, filed Nov. 24, 2020, which claims priority to United Kingdom Patent Application No. 1917101.6, filed Nov. 25, 2019, both of which are incorporated by reference in their entirety herein.

SEQUENCE LISTING

The Instant Application contains a Sequence Listing which has been submitted electronically in ASCII format and is hereby incorporated by reference in its entirety. Said ASCII copy, created on May 12, 2022 is named "NO20180US_ST25" and is 4,551 bytes in size.

FIELD OF THE INVENTION

The invention relates to methods of depleting host nucleic acid from a biological sample.

BACKGROUND TO THE INVENTION

Rapid and comprehensive infectious disease diagnostics are crucial for improved patient management and in the fight against antimicrobial resistance. Rapid diagnosis of life-threatening infectious diseases such as sepsis and pneumonia is paramount. These clinical syndromes have complex aetiologies and require pathogen recognition in challenging sample matrixes e.g. blood, sputum etc. Currently, the "gold standard" method for clinical diagnostics is microbial culture, which is labour intensive, has long turnaround times and poor clinical sensitivity. Currently available rapid molecular methods (e.g. PCR) improve turnaround time to result and sensitivity, but are limited by range and therefore rare pathogens and resistance markers can be problematic. The most applicable technology for rapid detection of microbial pathogens is nucleic acid amplification tests (NAATs). NAATs are available for sepsis diagnostics (e.g. Septifast®, Roche) but complexity of use and suboptimal performance have prevented their widespread adoption. Most of the NAATs for respiratory tract infections (RTIs) focus on the detection of respiratory viruses (e.g. Biofire Filmarray Respiratory Panel, Seegene RV15). Exceptions include the Curetis Unyvero® and Biofire® Pneumonia tests which are designed for community acquired and health care associated pneumonia. NAATs, however, are not comprehensive (e.g. the Curetis test only covers 90% of the top pathogens), seeking only a pre-set range of targets, meaning that less common pathogens will be missed. Consequently, NAAT diagnostics are an adjunct to standard bacteriology, not a replacement, and adoption is limited.

A paradigm shift in diagnostics technology is urgently required—a universal diagnostic method which can detect any pathogen (e.g. viral, bacterial, fungal) and antibiotic resistance. Agnostic/shotgun metagenomic sequencing has the potential to be the technology of choice to drive this shift. Shotgun metagenomic sequencing can detect and provide relative proportions of viruses, bacteria and fungi in a sample without any prior knowledge of the microbial community present, and is increasingly being used to investigate complex metagenomes in clinical samples.

So why is shotgun metagenomics not currently being widely applied to infection diagnosis? One reason is that next generation sequencing (NGS) has traditionally been expensive, complex to perform and difficult to analyse. The development of MinION® nanopore sequencing technology has changed the NGS landscape with cheap portable sequencers, rapid simple library preparation (15 mins) and automated real-time analysis tools. Another major barrier is the large amount of human DNA present in clinical samples, which is often several orders of magnitude greater than the pathogen DNA present. Blood is a particularly challenging matrix for NGS-based pathogen characterization due to the vast amount of human vs. pathogen nucleic acid (particularly DNA) present (ratio is typically $10^8:1$ to $10^9:1$, based upon $10^6$ leukocytes/ml [with ~6.6 pg DNA/cell] but as few as 1-10 colony forming units [CFU] of pathogen/ml [with ~5 fg DNA/cell]). A host DNA depletion of at least about $10^5$, potentially resulting in a human:pathogen DNA ratio of $10^3:1$, is required to facilitate NGS-based pathogen characterization in blood, a level of depletion (giving rise to pathogen nucleic acid enrichment) not achieved by methods disclosed in the art, such as commercially available pathogen DNA enrichment methods (QIAamp® DNA Microbiome Kit (Qiagen); NEBNext® Microbiome DNA Enrichment kit (NEB); MolYsis® Basic 5 kit (Molzym)). Additionally, many methods disclosed in the art are relatively slow, in part due to them deploying separate (sequential) host cell lysis and host nucleic acid degradation steps.

It is among the objects of this disclosure to address the aforementioned problems.

SUMMARY OF THE INVENTION

Accordingly, provided is a method for depleting host nucleic acid in a biological sample, said sample having been previously obtained from an animal host, said method comprising:
  a) adding to said sample a saponin, a DNase, and NaCl and/or KCl, to form a reaction mix, wherein the addition of said NaCl and/or KCl is sufficient to ensure a final concentration of NaCl and/or KCl in the reaction mix of at least 0.2M; and
  b) incubating the reaction mix at between 10° C. and 50° C.

Preferably, the DNase is a salt-active DNase, such as a DNase having the sequence of SEQ ID NO: 1 or of SEQ ID NO: 2, or an active variant thereof, and/or the method further comprises adding a Mg salt and/or a Mn salt to the sample, wherein the addition of said Mg salt and/or a Mn salt is sufficient to ensure a final concentration of Mg salt and/or Mn salt in the reaction mix of at least 1.0 mM.

Preferably, the saponin comprises a monodesmosidic saponin and/or the saponin comprises sapogenin, and preferably comprises a triterpenoid.

Preferably, the method further comprises the subsequent step of extracting remaining nucleic acid from the reaction mix. Preferably, the method further comprises the step of subjecting the extracted nucleic acid to a purification process and/or the step of amplifying the extracted nucleic acid. Further preferably, the method further comprises the step of conducting a nucleic acid amplification test on the extracted nucleic acid or, preferably, conducting a sequencing process on the extracted nucleic acid.

Preferably the biological sample is a sputum sample or a blood sample and/or the method results in at least a 10 fold, preferably at least a $10^2$ fold, preferably at least a $5 \times 10^2$ fold, preferably at least a $10^3$ fold, preferably at least a $5 \times 10^3$ fold, preferably at least a $10^4$ fold, preferably at least a $5 \times 10^4$ fold, most preferably at least a $10^5$ fold depletion of host DNA originally contained within the sample.

Also provided is a composition comprising NaCl and/or KCl at a concentration of at least 0.2M and a saponin. Preferably, the composition further comprises a Mg salt and/or a Mn salt at a concentration of at least 1.0 mM and/or a DNase, preferably wherein the DNase is a salt-active DNase, such as a DNase having the sequence of SEQ ID NO: 1 or of SEQ ID NO: 2, or an active variant thereof. Further preferably, the composition further comprises a biological sample, said sample having been previously obtained from an animal host, preferably wherein the biological sample is a sputum sample or a blood sample.

Also provided is a kit comprising i) a composition comprising NaCl and/or KCl at a concentration of at least 0.2M and ii) a composition comprising a saponin. Preferably, the kit further comprises iii) a composition comprising a DNase (preferably a salt-active DNase, such as a DNase having the sequence of SEQ ID NO: 1 or of SEQ ID No: 2, or an active variant thereof).

Also provided is a kit comprising i) a composition comprising NaCl and/or KCl at a concentration of at least 0.2M and a saponin and ii) a composition comprising a DNase (preferably a salt-active DNase, such as a DNase having the sequence of SEQ ID NO: 1 or of SEQ ID NO:2, or an active variant thereof).

DETAILED DESCRIPTION OF THE INVENTION

General

Provided herein is a method for depleting host nucleic acid (particularly RNA and/or, most preferably, DNA) in a biological sample, said sample having been previously obtained from an animal host, said method comprising a) adding to said sample a saponin, a DNase (any enzyme having DNase activity), and NaCl and/or KCl, to form a (liquid) reaction mix, wherein the addition of said NaCl and/or KCl is sufficient to ensure a final concentration of NaCl and/or KCl in the reaction mix of at least 0.2M, and b) incubating the reaction mix at between 10° C. and 50° C.

The animal host can be a vertebrate, e.g. a bird, a fish or, preferably, a mammal, most preferably a human. The host may, at the time of sample collection, be alive or dead.

The biological sample can be any sample that comprises animal cells (in tissue form or otherwise). Particular (e.g. clinical) samples of interest include bile, nail, nasal/bronchial lavage, bone marrow, stem cells derived from the body, bones, non-fetal products of conception, brain, breast milk, organs, pericardial fluid, buffy coat layer, platelets, cerebrospinal fluid, pleural fluid, cystic fluid, primary cell cultures, pus, saliva, skin, fetal tissue, fluid from cystic lesions, stomach contents, hair, teeth, tumour tissue, umbilical cord blood, mucus and stem cells. Particularly preferred samples include, though, joint aspirates, faeces, cerebrospinal fluid, urine and, especially, sputum and blood (including plasma). The sample might be taken directly into the disclosed method, or it might be processed, manipulated or altered prior to the disclosed method.

Preferably, the sample is in liquid form. An initial sample might need to be converted to liquid form before conducting the present methodology. A liquid sample might have a volume of between 10 µl and 100 ml, preferably between 10 µl and 50 ml, such as between 10 µl or 100 µl and 20 ml (e.g. 0.2 ml or 1 ml). Alternatively, a solid sample might be suspended in a (liquid) composition comprising one or more of the key, exogenous reaction mix components, saponin, DNase, and NaCl/KCl (and other optional exogenous components).

Reaction mix components saponin and DNase are discussed in later sections.

KCl and/or (preferably) NaCl are added in amounts that are sufficient to ensure a final concentration of NaCl and/or KCl in the reaction mix of at least 0.2M, i.e. without taking into account any NaCl and/or KCl that might be contained within the sample. For example, for a 200 µl sample, one might add a 200 µl composition comprising the saponin, the DNase, and the NaCl and/or KCl, with the NaCl and/or KCl concentration of that composition being 0.4M or more (e.g. 2.0M or more to ensure a final concentration of at least 1.0M). In other words, the reaction mix comprises at least 0.2M of exogenously added NaCl and/or KCl. Preferable concentrations (for NaCl alone, for KCl alone, or a mixture of NaCl and KCl) include at least 0.3M, at least 0.4M, at least 0.5M, at least 0.75M, at least 1.0M, at least 1.25M, at least 1.5M, at least 1.75M, at least 2.0M, at least 2.25M, at least 2.3M, at least 2.4M and at least 2.5M, up to e.g. 3.0M, 3.5M, 4.0M, 4.5M, 5.0M, or 5.5M. Preferred NaCl/KCl concentration ranges include between 0.2M and 0.3M and 5.0M, between 0.4M or 0.5M and 4.5M, between 1.0M or 1.5M and 4.5M, between 2.0M and 4.0M, and between 2.25M and 3.0M or 4.0M.

Preferably, particularly when the DNase is "HL-SAN DNase" or "M-SAN DNase" (see below), the method further comprises adding a Mn salt and/or (preferably) a Mg salt (preferably $MgCl_2$) to the sample, wherein the addition of said Mg salt and/or a Mn salt is sufficient to ensure a final concentration of Mg salt and/or Mn salt in the reaction mix of at least 1.0 mM (as explained above in relation to NaCl/KCl). Preferable concentrations include at least 2 mM, at least 3 mM, at least 4 mM, at least 5 mM, at least 10 mM, at least 15 mM, at least 20 mM, at least 25 mM, at least 30 mM, at least 35 mM or at least 40 mM, up to e.g. 60 mM, 100 mM, 200 mM, 500 mM, or 1.0M. Preferred Mg salt/Mn salt concentration ranges include between 1.0 mM or 10 mM and 1.0M, between 20 mM and 500 mM, and between 30 mM and 200 mM.

A further, optional, exogenous reaction mix component is a separate RNase (an enzyme having RNase activity), to (partially or completely) digest host RNA, particularly if the DNase does not additionally have RNase activity.

The method encompasses scenarios whereby the key, exogenous reaction mix components are added at different points in time, e.g. the saponin is added to the sample some time before the DNase is added to the sample, provided that all of such components (and any optional, further components) have been added and are present along with the sample in the reaction mix ahead of an incubation step. However, it is preferred that the NaCl/KCl (and any Mg/Mn salt) is added no later than the addition of the DNase. Furthermore, it is particularly preferred that the exogenous reaction mix components are added substantially simultaneously to the sample, e.g. there is no more than 5 min, such as no more than 2 min, no more than 60 s, or no more than 30 s, between the addition of the first and last (e.g. key) exogenous reaction mix components, or are added simultaneously to the sample, such as by adding to the sample a composition comprising the exogenous reaction mix components.

Preferably, the reaction mix is mixed (e.g. via pipetting) prior to and/or during the incubation step.

The reaction mix is incubated at between 10° C. and 50° C., preferably for at least 30 s, such as at least 60 s, at least 2 min, or at least 5 min. Preferably, the incubation lasts up to 10 min, such as up to 15 min, up to 20 m, up to 30 m, or up to 1 hr. Preferred incubation time ranges include 60 s to 30 min and 60 s to 20 min, e.g. 10 min. Preferred incubation temperature ranges include between 15° C. or 20° C. and 45° C. and between 25 or 30° C. and 40° C., e.g. 37° C. For part or all of the incubation, the reaction mix is preferably subject to mixing/shaking, at e.g. between 1 and 2000 rpm, preferably between 100 and 1500 rpm (e.g. at 500 rpm or 1000 rpm).

The saponin causes (selective) lysis of the host cells (and their interior membranes), releasing host nucleic acid such that it can be (partially or completely) digested by a DNase (which optionally has RNase activity as well as DNase activity). Nucleic acid within a non host cell or particle (e.g. pathogen) is essentially left intact (i.e. has not been significantly removed from the sample or digested) and identifiable, such that it can be subsequently collected and analysed and, in particular, identified (by e.g. sequencing or targeted PCR). A nucleic acid is identifiable e.g. if its sequence and/or biological origin can be ascertained.

Optionally, a buffering agent can be added to the reaction mixture, for example in circumstances where the reaction mix isn't otherwise at a pH of e.g. 7.0 to 9.5 (such as 7.5 to 9.5). The buffering agent can be used to maintain the pH of the reaction mixture at e.g. 7.0 to 9.5, such as (particularly for HL-SAN DNase) 7.5 to 9.5 (e.g. 8.0 or 8.5 to 9.0 or 9.5, preferably 9.0) or (particularly for M-SAN DNase) 7.0 to 9.0 (preferably 8.0).

Saponin

Saponins can be found e.g. in various plant species and can be grouped phenomenologically by the soap-like foam they produce when shaken in aqueous solutions. They act as non-ionic surfactants.

A saponin is an amphiphilic molecule, comprising a hydrophilic glycoside connected via a glycosidic bond(s) to a lipophilic aglycone group. Connection via one, two or more such bonds classifies saponins into mono-, bi- or polydesmosidic species. The aglycone group can be a sapogenin, i.e. containing a triterpene/triterpenoid or steroid. Preferably, the saponin used in the present technology comprises (or is) a monodesmosidic saponin, and/or comprises (or is) a sapogenin-based saponin (preferably comprising a triterpenoid). Preferably, for example, the saponin is (or comprises) a saponin having CAS number 8047-15-2 (e.g. saponin S0019 from Tokyo Chemical Industry™).

Preferably, the saponin is used in the reaction mix at a final concentration of at least 0.001% (weight by weight [w:w]), such as at least 0.01% (particularly for sputum), at least 0.05% (particularly for blood), at least 0.10%, or at least 0.50%, and up to 0.50%, 1%, 2%, 3%, 5% or 10%. Preferred concentration ranges include between 0.001% and 5%, between 0.01% and 3%, and between 0.05% and 1%, e.g. 0.1% (particularly for sputum) or 0.5% (particularly for blood). Minimum concentrations for blood tend to be approximately five times higher than for sputum.

DNase

The DNase can be an exonuclease or, preferably, an endonuclease, and/or have RNase activity.

Preferably, the DNase is a salt-active nuclease. A salt-active DNase is e.g. a DNase that 10 ng of which can provide a ΔAbs$_{260}$ (change in absorbance at 260 nm) of 0.0175 or more (e.g. 0.0875 or more, 0.175 or more, 0.35 or more, or 0.875 or more) in 30 minutes at 37° C., using 50 μg/ml calf thymus DNA, in a buffer containing 100 mM or more (up to e.g. 1M, 2M or 5M) NaCl and/or KCl (in e.g. a sample-free assay).

A preferred DNase is a DNase having the sequence of SEQ ID NO: 1, or an active variant thereof.

```
SEQ ID NO. 1:
APPSSFSKAKKEAVKIYLDYPTEFYCGCDITWKNKKKGIPELESCGYQV

RKQEKRASRIEWEHVVPAWQFGHQRQCWQKGGRKNCTRNDKQFKSMEAD

LHNLVPAIGEVNGDRSNFRFSQWNGSKGAFYGQCAFKVDFKGRVAEPPA

QSRGAIARTYLYMNNEYKFNLSKAQRQLMEAWNKQYPVSTWECTRDERI

AKIQGNHNQFVYKACTK
```

A DNase having the sequence of SEQ ID NO: 1 is also known as HL-SAN DNase (heat labile salt active nuclease, which can e.g. be supplied by Arcticzymes™). HL-SAN DNase is an endonuclease with both DNase and RNase activity. HL-SAN DNase corresponds to *Vibrio salmonicida* Endonuclease I (VsEndA), without its initial N-terminal signal peptide and featuring an S to E substitution at the S that is positioned in the wild-type sequence immediately N-terminal to a highly conserved FYCGC pentapeptide motif.

A further preferred DNase is a DNase having the sequence of SEQ ID NO: 2, or an active variant thereof.

```
SEQ ID NO. 2:
APISFSHAKNEAVKIYRDHPVEFYCGCEIRWQGKKGIPDLESCGYQVRK

NENRASRIEWEHVVPAWQFGHQLQCWQQGGRKNCTRTSPEFNQMEADLH

NLVPAIGEVNGDRSNFRFSQWNSKGAFYGQCAFKVDFKGRVAEPPAQSR

GAIARTYLYMSEQYGLRLSKAQNQLMQAWNNQYPVSEWECVRDQKIEKV

QNSNRFVREQCPN
```

A DNase having the sequence of SEQ ID NO: 2 is also known as M-SAN DNase (which can e.g. be supplied by Arcticzymes™). M-SAN DNase is an endonuclease with both DNase and RNase activity. M-SAN DNase corresponds to *Vibrio cholerae* Endonuclease I (VcEndA), without its initial N-terminal signal peptide and featuring an S to E substitution at the S that is positioned in the wild-type sequence immediately N-terminal to a highly conserved FYCGC pentapeptide motif.

HL-SAN DNase and M-SAN DNase provide for highly effective degradation (digestion) of host cell nucleic acid (especially DNA), particularly at high salt concentrations.

An active variant of HL-SAN DNase is a variant that retains e.g. at least 10%, preferably at least 25%, preferably at least 50%, preferably at least 60%, preferably at least 70%, preferably at least 80%, preferably at least 90%, preferably at least 95% of HL-SAN DNase. Activity can be measured e.g. via increase in absorbance (e.g. at 260 nm), for example in a sample-free assay, over a specified period (e.g. 30 minutes) at a specified temperature (e.g. 37° C.), using (e.g. 50 μg/ml) (e.g. calf thymus) DNA in a suitable buffer (e.g. consisting of 25 mM Tris-HCl, pH 8.5 (25° C.), 5 mM MgCl$_2$, 500 mM NaCl).

An active variant of M-SAN DNase is a variant that retains e.g. at least 10%, preferably at least 25%, preferably at least 50%, preferably at least 60%, preferably at least 70%, preferably at least 80%, preferably at least 90%, preferably at least 95% of M-SAN DNase. Activity can be measured e.g. via increase in absorbance (e.g. at 260 nm), for example in a sample-free assay, over a specified period (e.g. 30 minutes) at a specified temperature (e.g. 37° C.), using (e.g. 50 µg/ml) (e.g. calf thymus) DNA in a suitable buffer (e.g. consisting of 25 mM Tris-HCl, pH 7.2 (37° C.), 2.5 or 5 mM $MgCl_2$, 150 or 175 mM NaCl).

"An active variant thereof" includes within its scope a fragment of HL-SAN DNase or M-SAN DNase. Preferably, a fragment of HL-SAN DNase or M-SAN DNase is selected that is at least 10% of the length of the HL-SAN or M-SAN DNase protein sequence, preferably at least 20%, preferably at least 30%, preferably at least 40%, preferably at least 50%, preferably at least 60%, preferably at least 70%, preferably at least 80%, preferably at least 90% and most preferably at least 95% of the length of the HL-SAN or M-SAN DNase protein sequence.

"An active variant thereof" also includes within its scope a protein sequence that has homology with the HL-SAN or M-SAN DNase protein sequence, such as at least 50% identity, preferably at least 60%, preferably at least 70%, preferably at least 80%, preferably at least 85%, preferably at least 90%, preferably at least 95%, preferably at least 97%, and most preferably at least 99% identity, for example over the full HL-SAN or M-SAN DNase sequence or over a region of contiguous amino acid residues representing 10% of the length of the HL-SAN or M-SAN DNase protein sequence, preferably at least 20%, preferably at least 30%, preferably at least 40%, preferably at least 50%, preferably at least 60%, preferably at least 70%, preferably at least 80%, preferably at least 90% and most preferably at least 95% of the length of the HL-SAN or M-SAN DNase protein sequence. Methods of measuring protein homology are well known in the art and it will be understood by those of skill in the art that in the present context, homology is calculated on the basis of amino acid identity (sometimes referred to as "hard homology").

The homologous active HL-SAN or M-SAN DNase variant typically differs from the HL-SAN or M-SAN DNase protein sequence by substitution, insertion or deletion, for example from 1, 2, 3, 4, 5 to 8 or more substitutions, deletions or insertions. The substitutions are preferably 'conservative', that is to say that an amino acid may be substituted with a similar amino acid, whereby similar amino acids share one of the following groups: aromatic residues (F/H/W/Y), non-polar aliphatic residues (G/A/P/I/L/V), polar-uncharged aliphatics (C/S/T/M/N/Q) and polar-charged aliphatics (D/E/K/R). Preferred sub-groups comprise: G/A/P; I/L/V; C/S/T/M; N/Q; D/E; and K/R.

The HL-SAN or M-SAN DNase or active variant thereof (as described above) may have any number of amino acid residues added to the N-terminus and/or the C-terminus provided that the protein retains DNase activity. Preferably, no more than 300 amino acid residues are added to either or both ends, more preferably no more than 200 amino acid residues, preferably no more than 150 amino acid residues, preferably no more than 100 amino acid residues, preferably no more than 80, 60 or 40 amino acid residues, most preferably no more than 20 or 10 or 5 amino acid residues.

Preferably, the DNase (e.g. HL-SAN DNase or active variant thereof) is used in the reaction mix at a final concentration of at least 0.01 units per µl (U/µl), such as at least 0.05 U/µl, at least 0.1 U/µl, or at least 0.5 U/µl, and up to 1 U/µl, 5 U/µl, or 10 U/µl. Preferred concentration ranges include between 0.01 U/µl or 0.05 U/µl and 5 U/µl, and between 0.1 U/µl and 1 U/µl, e.g. 0.5 U/µl. One Unit is optionally defined as an increase in absorbance at 260 nm of 1 A in 30 minutes at 37° C., using 50 µg/ml calf thymus DNA in a buffer, consisting of e.g. a) 25 mM Tris-HCl, pH 8.5 (25° C.), 5 mM $MgCl_2$, 500 mM NaCl (particularly for HL-SAN DNase) or b) 25 mM Tris-HCl, pH 7.2 (37° C.), 2.5 or 5 mM $MgCl_2$, 150 or 175 mM NaCl (particularly for M-SAN DNase).

Further Steps

Preferably, the method further comprises the step of extracting remaining (preferably non host) nucleic acid from the reaction mix (or aliquot thereof). Part or all of the remaining nucleic acid (particularly non host nucleic acid) will be intact and identifiable.

Typically, the extraction process will involve a centrifugation step to collect, in particular, non host cells/particles (e.g. pathogens) (virus particles and/or, in particular, bacterial and/or non-animal (e.g. non-mammalian) (e.g. unicellular) eukaryotic cells, such as fungi), from which the nucleic acid can be obtained. Centrifugation conditions can be selected such that bacterial and non-animal cells, but not virus particles, are pelleted, or such that virus particles are pelleted in addition to bacterial and non-animal cells. If the former, standard virus detection tests could be performed on the supernatant. (Indeed, prior to step a) of the present method, one might centrifuge a clinical sample, keep the cell-containing pellet (for the method of the current technology), and keep the supernatant for virus detection using standard procedures, with or without enrichment using the present technology.)

Nucleic acid can be obtained from the pathogen(s) using methods known in the art, and might involve the addition of a lysis buffer, a lytic enzyme(s) (degrading or abrogating cell membranes, cell walls and/or viral capsids), and/or a protease, e.g. proteinase K. Preferred lytic enzymes include lysozyme, mutanolysin, lysostaphin, chitinase and lyticase.

Optionally, the extracted nucleic acid (or aliquot thereof) is subject to a purification process, such as one known in the art. During purification of DNA, RNase is optionally used to facilitate the optimisation of subsequent DNA sequencing. However, RNase is omitted from any purification step if non host (e.g. pathogen) RNA extraction is of interest (for e.g. subsequent RNA sequencing) (and a DNase might be used to assist with purification). Preferably, extracted nucleic acid (or aliquot thereof) is subject to an amplification process, such as whole genome amplification, to increase the copy number/quantity of the nucleic acid, particularly where the biological sample is a blood sample. For RNA, this might involve direct amplification or conversion of RNA to cDNA, followed by amplification of cDNA.

Preferably, the method further comprises the step of conducting a nucleic acid amplification test (e.g. targeted PCR amplification process, isothermal amplification, nucleic acid sequence-based amplification (NASBA)) on the extracted nucleic acid (RNA, DNA or cDNA) (or aliquot thereof) or, preferably, conducting a sequencing process on the extracted nucleic acid (or aliquot thereof), such as (e.g. short or long read) DNA or RNA sequencing, using e.g. nanopore or Illumina® sequencing.

Preferably, nucleic acid (particularly host nucleic acid) previously digested will not be amplified by any amplification process and/or (in particular) sequenced by any sequencing process.

Preferable outcome features of the present technology include a fold depletion of host DNA from within a biological sample from a mammalian host of 10 or greater, $10^2$ or greater, $5 \times 10^2$ or greater, $10^3$ or greater, $5 \times 10^3$ or greater, $10^4$ or greater, $5 \times 10^4$ or greater, such as $10^5$ or greater (e.g. $10^6$ or greater). It is particularly preferred that host nucleic acid (e.g. DNA) is undetectable (e.g. via qPCR) following deployment of the method of the invention. For example, preferable outcome features include a fold depletion of host DNA from within a sputum sample from a mammalian host of $5\times10^2$ or greater, $10^3$ or greater, $5\times10^3$ or greater, or $10^4$ or greater, or a fold depletion of host DNA from within a blood sample from a mammalian host of $5\times10^3$ or greater, $10^4$ or greater, $5\times10^4$ or greater, or $10^5$ or greater.

The new method provides host nucleic acid depletion that is rapid, and highly effective (e.g. circa $10^3$ or $10^4$ depletion in sputum) and selective (i.e. leaving non host nucleic acid intact), leading to excellent non host (e.g. pathogen) nucleic acid enrichment, sufficient for subsequent sequencing-based (e.g. next-generation sequencing [NGS] based) (e.g. pathogen) diagnostics. In more general terms, the rapid and selective depletion of host nucleic acid enables enrichment of non host nucleic acid, and hence improved identification of non host organisms. This technology is thus applicable to fields other than medical microbiology, such as biological research, veterinary medicine/diagnostic, and agriculture/food safety.

The present method provides conditions in which the lysis and nucleic acid depletion (e.g. digestion) steps can be carried out partially, substantially, essentially or entirely in parallel (i.e. simultaneously), hence being referred to as a 'one-step' and/or 'one-pot' depletion method, in contrast to prior art methods that deploy separate lysis and depletion steps that are sequential/in-series ('two-step' methods). This arrangement significantly reduces the time needed to complete host nucleic acid depletion, yet does so with highly effective and selective depletion outcomes. The conditions that allow this—combining saponin and DNase in "high salt"—were surprising, not least because it was surprising that saponin remains active in "high salt" conditions and that DNase remains active in the presence of saponin (which might have been expected to adversely affect the enzyme's conformation and hence activity).

Compositions

In the present method, the exogenous reaction mix components can be added individually/separately to the biological sample (as defined above). However, a range of ("premixed", liquid) compositions can be prepared and are herein provided, along with the reaction mix itself.

For example, provided is a composition comprising a saponin and a DNase. This may optionally e.g. be combined with NaCl/KCl (giving NaCl/KCl concentration of at least 0.2M) (with or without addition of Mg salt/Mn salt to give concentration of at least 1.0 mM) before or after addition to the sample.

Preferably, however, is a composition comprising NaCl and/or KCl at a concentration of at least 0.2M and a saponin. Other exogenous components and the sample can then be added/mixed, in any order, to provide a reaction mix. Hence, preferably, the composition further comprises a Mg salt and/or a Mn salt at a concentration of at least 0.2 mM, and/or a DNase, and/or a biological sample. Particularly preferred is a composition (a "pre-reaction mix") comprising said NaCl/KCl (and optionally said Mg salt/Mn salt), said saponin and said DNase; this composition can be added in one step to the sample to form the reaction mix. Typically, the DNase will be added last to the pre-reaction mix.

Preferable features of these compositions can be found in the above sections, in particular in relation to e.g. the nature and concentration of the various salts, of the saponin, and of the DNase.

Kits

Also provided is a kit (e.g. a kit of parts) comprising i) a (liquid) composition comprising NaCl and/or KCl at a concentration of at least 0.2M and ii) a composition comprising a saponin. The compositions are separate from each other (e.g. are contained in separate [e.g. sealed] containers) but are associated with each other (e.g. by physical means) into a kit e.g. all contained within a packaged product. The composition comprising a saponin can be solid or liquid. Preferably, the kit further comprises iii) a (separate) composition comprising a DNase. Optionally, composition i) or (particularly when in liquid form) composition ii) further comprises a Mg salt and/or a Mn salt at a concentration of at least 1.0 mM.

Also provided is a kit (as defined above) comprising i) a composition comprising NaCl and/or KCl at a concentration of at least 0.2M and a saponin and ii) a composition comprising a DNase. Optionally, composition i) further comprises a Mg salt and/or a Mn salt at a concentration of at least 1.0 mM.

Preferable features of the compositions of these kits can be found in the above sections, in particular in relation to e.g. the nature and concentration of the various salts, of the saponin, and of the DNase.

General

Please note that wherever the term 'comprising' is used herein we also contemplate options wherein the terms 'consisting of' or 'consisting essentially of' are used instead. In addition, please note that the term 'protein' used herein can be used interchangeably with the term 'polypeptide'. Furthermore, any and all liquid compositions as described above can be aqueous solutions. Note too that whenever the phrase "at least" is used for a value X, this is a disclosure of each of two alternative options of a) X and b) more than X (e.g. "at least 0.2M" is equivalent to "0.2M or more than 0.2M").

Examples

Here, we describe the process of developing a simple and rapid ("one-step") and highly efficient human DNA depletion method to enable downstream metagenomic sequencing (and other molecular applications e.g. PCR) for e.g. the detection and identification of pathogens and associated antibiotic resistance markers.

For efficient, rapid and cost effective metagenomic diagnosis of infection, human DNA depletion or pathogen DNA enrichment is essential. We took an approach involving human DNA depletion, focussing on differential lysis of human cells (using a saponin), and removal of human DNA (using a DNase), leaving intact e.g. human pathogens for further analysis.

An undepleted control (UC) was added in to every experiment, which was DNA extracted from 200 µl of sputum/blood without performing the depletion procedure. Clinical sputum samples were processed and 16S rRNA gene fragment qPCR was used to ensure that pathogen DNA was not inadvertently degraded during the procedure.

Subsequently, DNA was extracted as follows (unless otherwise stated in the experimental procedure):

1. Bacterial lysis buffer (to a maximum volume of 700 µl) was added to the treated sample. To the UC 500 µl of bacterial lysis buffer was added. Samples were transferred to a bead-beating tube (purple lid—matrix lysing E tubes (MP Biomedicals LLP)) and bead-beat 3 min at 50 o/s (Qiagen TissueLyser LT).
2. All samples were centrifuged at max speed (~20,000× g) for 1 minute. Clear supernatant (2×200 µl) transferred to a new tube with 20 µl of Proteinase K and mixed by vortexing.
3. All samples were incubated at 65° C. for 5 min at 1000 rpm.

4. Followed by purification on the MagNAPure®.

For all experiments, human and bacterial nucleic acid was quantified using qPCR. A hydrolysis probe assay was designed to detect human targeting the RNA polymerase II gene. A 16S rRNA qPCR assay was used for the relative quantification of bacteria in the samples. All qPCR results are presented as quantification cycle (Cq) values (this represents the cycle at which the fluorescence signal increases above background which is directly related to the quantity of starting template concentration). The relative concentration of DNA in samples was calculated using the ΔCq (every 3.3 cycles represents a 10-fold difference in concentration; the higher the Cq value the less starting template DNA was present in the sample).

Comparative Example—Two-Step Protocol (Sputum)

1. Centrifuge 200 µl of sputum at 12,000×g for 5 min.
2. Discard the supernatant (do not disturb pellet, <50 µl supernatant remaining) and re-suspend pellet in 200 µl of PBS. Mix very well by pipetting up and down.
3. Add 20 µl of 1% Saponin (S0019 from Tokyo Chemical Industry™), mix well by pipetting and incubate at 37° C. for 15 min at 1000 rpm.
4. Centrifuge at 12,000×g for 5 min.
5. Discard the supernatant (do not disturb the pellet) and re-suspend pellet in 200 µl PBS by pipetting.
6. Add 200 µl of HLSAN buffer (in molecular water: 5.5M NaCl and 100 mM $MgCl_2$) and 10 µl of HLSAN DNase (at 25 U/µl, sourced from Arcticzymes™). Vortex briefly.
7. Incubate at 37° C. for 10 min at 1000 rpm.
8. Add 1.5 ml of PBS and centrifuge at 12,000×g for 5 min.
9. Discard the supernatant and resuspend in 1.5 ml of PBS by pipetting.
10. Centrifuge at 12,000×g for 5 min.
11. Discard the supernatant and resuspend pellet in 600 µl of BLB (bacterial lysis buffer from Roche™).
12. Transfer to a bead-beating tube (purple lid—matrix lysing E tubes). Bead-beat 3 min at 50 o/s.
13. Centrifuge at max speed (~20,000×g) for 1 minute.
14. Transfer 2×150 µl of clear supernatant to a new tube with 100 µl of BLB and 20 µl of Proteinase K.
15. Vortex briefly and incubate at 65° C. for 5 min.
16. DNA extraction.

Example 1—One-Step Protocol (Sputum)

1. To 200 µl of sputum add 40 µl of 1% Saponin (details above), 200 µl of HLSAN buffer (in molecular water: 5.5M NaCl and 100 mM $MgCl_2$) and 10 µl of HLSAN DNase (details above), mix well by pipetting and incubate at 37° C. for 10 min at 1000 rpm.
2. Add 1 ml of PBS and centrifuge at 12,000×g for 3 min.
3. Resuspend pellet in 700 µl of BLB (bacterial lysis buffer from Roche™).
4. Transfer to a bead-beating tube (purple lid—matrix lysing E tubes). Bead-beat 3 min at 50 o/s.
5. Centrifuge at max speed (~20,000×g) for 1 minute.
6. Transfer 2×200 µl of clear supernatant to a new tube with 20 µl of Proteinase K.
7. Vortex briefly and incubate at 65° C. for 5 min 1000 rpm.
8. DNA extraction.

Human DNA depletion was monitored using a qPCR assay alongside 16S qPCR assay to observe bacterial loss/gain (40 qPCR cycles):

| Sample | Human qPCR assay (Cq) | Human DNA depletion (delta Cq) | 16S qPCR assay (Cq) | 16S DNA loss/gain (delta Cq) |
|---|---|---|---|---|
| UC (no depletion) | 21.64 | — | 20.85 | — |
| Two-step method | 30.66 | 9.02 (519-fold depletion) | 17.58 | 3.27 (10-fold gain) |
| One-step method | 30.82 | 9.17 (576-fold depletion) | 17.50 | 3.35 (10-fold gain) |

Conclusion: Combining the saponin and nuclease steps together (retaining the nuclease's high salt buffer) gave equivalent levels of host DNA depletion without bacterial DNA loss. Therefore, this streamlined combined (one-step) method was repeated and a sample sequenced using the ONT Flongle® platform.

Example 2—One-Step Protocol (Sputum) Followed by Nanopore Sequencing

The use of the one-step/one-pot host DNA depletion method (Example 1) for clinical metagenomics will require downstream DNA sequencing. Therefore, a fresh clinical sputum sample was processed using this method (Example 1) and sequenced using the Flongle sequencing platform from Oxford Nanopore Technologies (ONT)®.

Human DNA depletion was again monitored using a qPCR assay alongside a 16S qPCR assay to observe bacterial loss/gain (40 qPCR cycles):

| Sample | Human qPCR assay (Cq) | Human DNA depletion (delta Cq) | 16S qPCR assay (Cq) | 16S DNA loss/gain (delta Cq) |
|---|---|---|---|---|
| UC (no depletion) | 22.48 | — | 20.71 | — |
| One-step method | 33.72 | 11.24 (>2419 fold depletion) | 19.83 | 0.88 (1.8-fold gain) |

The pathogen *Pseudomonas aeruginosa* was identified within 2 hours of sequencing and dominated the classified reads:

Total reads: 51,000
Classified: 47,703
Unclassified: 3,297
Human: 289 (0.6% of classified reads)
*P. aeruginosa:* 29,612 (62.1% of classified reads)

Conclusion:

We have developed a rapid one-step/one-pot host DNA depletion method (~13 min) capable of ~$10^3$ fold host DNA depletion in sputum with no bacterial loss. This can be applied for the efficient diagnosis of pathogens in human/animal samples using PCR or sequencing (clinical metagenomics).

Example 3—One-Step Protocol (Blood)

The one-step protocol was also tested in blood spiked with *E. coli* (one of the most common sepsis causing pathogens). For all experiments in blood, human and *E. coli* nucleic acid was quantified using qPCR with specific hydrolysis probe assays (single copy gene targets; RNA polymerase II and cyaA respectively).

1. To 200 μl of blood add 40 μl of Saponin (1% or 5%), 200 μl of HLSAN buffer (in molecular water: 5.5M NaCl and 100 mM MgCl$_2$) and 10 μl of HLSAN DNase, mix well by pipetting and incubate at 37° C. for 10 min at 1000 rpm.
2. Add 1 ml of PBS and centrifuge at 12,000×g for 3 min.
3. Resuspend pellet in 700 μl of BLB (bacterial lysis buffer from Roche™).
4. Transfer to a bead-beating tube (purple lid—matrix lysing E tubes). Bead-beat 3 min at 50 o/s.
5. Centrifuge at max speed (~20,000×g) for 1 minute.
6. Transfer 2×200 μl of clear supernatant to a new tube with 20 μl of Proteinase K.
7. Vortex briefly and incubate at 65° C. for 5 min 1000 rpm.
8. DNA extraction.

The results from qPCR (40 cycles) as shown in the following table:

| Sample | Human qPCR assay (Cq) | Human DNA depletion (delta Cq) | E. coli qPCR assay (Cq) | E. coli DNA loss/gain (delta Cq) |
| --- | --- | --- | --- | --- |
| UC (no depletion) | 23.22 | — | 20.22 | — |
| One-step method (final saponin concentration 0.1%) | 31.49 | 8.27 (309-fold depletion) | 19.72 | 0.5 (1.4-fold gain) |
| One-step method (final saponin concentration 0.5%) | Undetected | >16 (>100,000-fold depletion) | 19.86 | 0.4 (1.3-fold gain) |

Conclusion: the rapid one-step/one-pot host DNA depletion method with saponin is capable of ~10$^5$ fold host DNA depletion in blood with no bacterial loss.

Example 4—One-Step Protocol (Sputum) with Salt Variation

The one-step protocol was repeated, in sputum samples, with salt variations in the HLSAN buffer:

1. To 200 μl of sputum add 40 μl of 1% Saponin, 200 μl of HLSAN buffer (in molecular water: 1-4M KCl and 100 mM MgCl$_2$ or in molecular water 1-5M (NH$_4$)$_2$SO$_4$ and 100 mM MgCl$_2$) and 10 μl of HLSAN DNase, mix well by pipetting and incubate at 37° C. for 10 min at 1000 rpm.
2. Add 1 ml of PBS and centrifuge at 12,000×g for 3 min.
3. Resuspend pellet in 700 μl of BLB (bacterial lysis buffer from Roche™).
4. Transfer to a bead-beating tube (purple lid—matrix lysing E tubes). Bead-beat 3 min at 50 o/s.
5. Centrifuge at max speed (~20,000×g) for 1 minute.
6. Transfer 2×200 μl of clear supernatant to a new tube with 20 μl of Proteinase K.
7. Vortex briefly and incubate at 65° C. for 5 min 1000 rpm.
8. DNA extraction.

Human DNA depletion was monitored using a qPCR assay alongside 16S qPCR assay to observe bacterial loss/gain:

| Sample | Human qPCR assay (Cq) | Human DNA depletion (delta Cq) | 16S qPCR assay (Cq) | 16S DNA loss/gain (delta Cq) |
| --- | --- | --- | --- | --- |
| UC (no depletion) | 18.71 | — | 19.48 | — |
| 5.5M NaCl buffer (one-step method) | 30.99 | 12.28 (4,973-fold depletion) | 16.60 | 2.88 (7.4-fold gain) |
| 1M KCl buffer (one-step method) | 29.10 | 10.39 (1,342-fold depletion) | 15.74 | 3.74 (13.4-fold gain) |
| 2M KCl buffer (one-step method) | 30.08 | 11.37 (2,647-fold depletion) | 15.62 | 3.86 (14.5-fold gain) |
| 3M KCl buffer (one-step method) | 30.61 | 11.90 (3,822-fold depletion) | 16.14 | 3.34 (10.1-fold gain) |
| 4M KCl buffer (one-step method) | 30.89 | 12.18 (4,640-fold depletion) | 16.54 | 2.94 (7.7-fold gain) |

| Sample | Human qPCR assay (Cq) | Human DNA depletion (delta Cq) | 16S qPCR assay (Cq) | 16S DNA loss/gain (delta Cq) |
| --- | --- | --- | --- | --- |
| UC (no depletion) | 19.61 | — | 16.75 | — |
| 5.5M NaCl buffer (one-step method) | 30.53 | 10.92 (1,938-fold depletion) | 13.13 | 3.62 (12.3-fold gain) |
| 1M (NH$_4$)$_2$SO$_4$ buffer (one-step method) | 27.98 | 8.37 (331-fold depletion) | 13.04 | 3.71 (13.1-fold gain) |
| 2M (NH$_4$)$_2$SO$_4$ buffer (one-step method) | 29.49 | 9.88 (942-fold depletion) | 13.07 | 3.68 (12.8-fold gain) |
| 3M (NH$_4$)$_2$SO$_4$ buffer (one-step method) | 29.04 | 9.43 (690-fold depletion) | 13.01 | 3.74 (13.4-fold gain) |
| 4M (NH$_4$)$_2$SO$_4$ buffer (one-step method) | 28.48 | 8.87 (468-fold depletion) | 14.70 | 2.05 (4.1-fold gain) |
| 5M (NH$_4$)$_2$SO$_4$ buffer (one-step method) | 25.69 | 6.08 (68-fold depletion) | 13.43 | 3.32 (10-fold gain) |

Conclusion: Replacing the NaCl in the HL-SAN buffer with KCl produced equivalent levels of host depletion without bacterial loss in the one-step protocol. Replacing the NaCl in the HL-SAN buffer with ammonium sulfate produced lower levels of host depletion, albeit without bacterial loss, in the one-step protocol.

Example 5—One-Step Protocol (Sputum) with Variation of DNase

The one-step protocol was repeated, in sputum samples, with a different DNase, specifically M-SAN DNase (at 27.6 U/μl, sourced from Arcticzymes™):

1. To 200 μl of sputum add 40 μl of 1% Saponin, 200 μl of M-SAN buffer (in molecular water: 2× buffer i.e. 350 mM NaCl and 5 mM MgCl$_2$ or 10× buffer i.e. 1.75M NaCl and 12.5 mM MgCl$_2$) and 10 μl of M-SAN DNase, mix well by pipetting and incubate at 37° C. for 10 min at 1000 rpm.
2. Add 1 ml of PBS and centrifuge at 12,000×g for 3 min.
3. Resuspend pellet in 700 μl of BLB (bacterial lysis buffer from Roche™).
4. Transfer to a bead-beating tube (purple lid—matrix lysing E tubes). Bead-beat 3 min at 50 o/s.
5. Centrifuge at max speed (~20,000×g) for 1 minute.

6. Transfer 2×200 μl of clear supernatant to a new tube with 20 μl of Proteinase K.
7. Vortex briefly and incubate at 65° C. for 5 min 1000 rpm.
8. DNA extraction.

Human DNA depletion was monitored using a qPCR assay alongside 16S qPCR assay to observe bacterial loss/gain:

| Sample | Human qPCR assay (Cq) | Human DNA depletion (delta Cq) | 16S qPCR assay (Cq) | 16S DNA loss/gain (delta Cq) |
|---|---|---|---|---|
| UC (no depletion) | 18.71 | — | 19.48 | — |
| HL-SAN DNase (one-step method) | 30.99 | 12.28 (4,973-fold depletion) | 16.60 | 2.88 (7.4-fold gain) |
| M-SAN DNase & 2× buffer (one-step method) | 25.15 | 6.44 (86.8-fold depletion) | 17.40 | 2.08 (4.2-fold gain) |
| M-SAN DNase & 10× buffer (one-step method) | 31.43 | 12.72 (6,747-fold depletion) | 16.89 | 2.59 (6.0-fold gain) |

Repeated with a different sputum sample:

| Sample | Human qPCR assay (Cq) | Human DNA depletion (delta Cq) | 16S qPCR assay (Cq) | 16S DNA loss/gain (delta Cq) |
|---|---|---|---|---|
| UC (no depletion) | 23.38 | — | 12.31 | — |
| HL-SAN DNase (one-step method) | 33.67 | 10.29 (1,252-fold depletion) | 13.98 | 1.67 (3.2-fold gain) |
| M-SAN DNase & 10× buffer (one-step method) | 33.68 | 10.3 (1,261-fold depletion) | 13.83 | 1.52 (2.9-fold gain) |

Conclusion: M-SAN DNase proved to be a suitable alternative to HL-SAN DNase, at least when using 5× recommended salt in the DNase buffer for M-SAN DNase (increased depletion by 6.3 Cq (78.8-fold) with no loss of bacteria compared with using 2× recommended salt in the buffer).

Further Comparative Example 1—One-Step Protocol (Sputum) with Variation of DNase Conditions (MNase in MNase Buffer)

The one-step protocol was repeated, but using Micrococcal Nuclease (MNase) in MNase buffer (including $CaCl_2$ and Tris-HCl):
1. To 200 μl of sputum add 40 μl of 1% Saponin, 200 μl of MNase buffer (in molecular water: 2× buffer i.e. 10 mM $CaCl_2$ and 100 mM Tris-HCl pH 8.0 or 10× buffer i.e. 50 mM $CaCl_2$ and 500 mM Tris-HCl pH 8.0) and 2 μl of MNase (at >100 U/μl, sourced from Thermo Scientific™), mix well by pipetting and incubate at 37° C. for 10 min at 1000 rpm.
2. Add 1 ml of PBS and centrifuge at 12,000×g for 3 min.
3. Resuspend pellet in 700 μl of BLB (bacterial lysis buffer from Roche®).
4. Transfer to a bead-beating tube (purple lid—matrix lysing E tubes). Bead-beat 3 min at 50 o/s.
5. Centrifuge at max speed (~20,000×g) for 1 minute.
6. Transfer 2×200 μl of clear supernatant to a new tube with 20 μl of Proteinase K.
7. Vortex briefly and incubate at 65° C. for 5 min 1000 rpm.
8. DNA extraction.

Human DNA depletion was monitored using a qPCR assay alongside 16S qPCR assay to observe bacterial loss/gain:

| Sample | Human qPCR assay (Cq) | Human DNA depletion (delta Cq) | 16S qPCR assay (Cq) | 16S DNA loss/gain (delta Cq) |
|---|---|---|---|---|
| UC (no depletion) | 19.57 | — | 19.65 | — |
| HL-SAN DNase (one-step method) | 32.17 | 12.6 (6,208-fold depletion) | 14.62 | 5.03 (32.7-fold gain) |
| MNase & 2× buffer (one-step method) | 24.24 | 4.67 (25.5-fold depletion) | 14.48 | 5.17 (36-fold gain) |
| MNase & 10× buffer (one-step method) | 21.69 | 2.12 (4.3-fold depletion) | 14.77 | 4.88 (29.4-fold gain) |

Conclusion: using MNase in $CaCl_2$ and Tris-HCl buffer instead of HL-SAN DNase in NaCl or KCl buffer resulted in insufficient host depletion. There was no loss of bacteria.

Further Comparative Example 2—One-Step Protocol (Sputum) with Variation of DNase Conditions (Benzonase in Benzonase Buffer)

The one-step protocol was repeated, but using Benzonase in Benzonase buffer (including $Mg^{2+}$):
1. To 200 μl of sputum add 40 μl of 1% Saponin, 200 μl of Benzonase buffer (in molecular water: 2× buffer i.e. 4 mM $Mg^{2+}$ or 10× buffer i.e. 20 mM $Mg^{2+}$) and 2 μl of Benzonase (at ≥250 U/μl, sourced from Sigma-Aldrich®), mix well by pipetting and incubate at 37° C. for 10 min at 1000 rpm.
2. Add 1 ml of PBS and centrifuge at 12,000×g for 3 min.
3. Resuspend pellet in 700 μl of BLB (bacterial lysis buffer from Roche™).
4. Transfer to a bead-beating tube (purple lid—matrix lysing E tubes). Bead-beat 3 min at 50 o/s.
5. Centrifuge at max speed (~20,000×g) for 1 minute.
6. Transfer 2×200 μl of clear supernatant to a new tube with 20 μl of Proteinase K.
7. Vortex briefly and incubate at 65° C. for 5 min 1000 rpm.
8. DNA extraction.

Human DNA depletion was monitored using a qPCR assay alongside 16S qPCR assay to observe bacterial loss/gain:

| Sample | Human qPCR assay (Cq) | Human DNA depletion (delta Cq) | 16S qPCR assay (Cq) | 16S DNA loss/gain (delta Cq) |
|---|---|---|---|---|
| UC (no depletion) | 19.57 | — | 19.65 | — |
| HL-SAN DNase (one-step method) | 32.17 | 12.6 (6,208-fold depletion) | 14.62 | 5.03 (32.7-fold gain) |
| Benzonase & 2× buffer (one-step method) | 24.83 | 5.26 (38.3-fold depletion) | 14.68 | 4.97 (31.3-fold gain) |
| Benzonase & 10× buffer (one-step method) | 24.78 | 5.21 (37-fold depletion) | 14.45 | 5.2 (36.8-fold gain) |

Conclusion: using Benzonase in $Mg^{2+}$ buffer in place of HL-SAN DNase in NaCl or KCl buffer resulted in insufficient host depletion. There was no loss of bacteria.

The invention claimed is:

1. A method for depleting host nucleic acid in a biological sample, said biological sample having been previously obtained from an animal host, wherein said biological sample comprises animal host cells, comprising:
   a) adding to said biological sample a saponin, a DNase, and NaCl and/or KCl, to form a reaction mix, wherein the addition of said NaCl and/or KCl is sufficient to ensure a final concentration of NaCl and/or KCl in the reaction mix of at least 0.2M; and
   b) incubating the reaction mix at between 10° C. and 50° C.;
   wherein, in said method, lysis of host cells and DNase degradation of host nucleic acid occur at least partially in parallel.

2. The method according to claim 1, wherein the DNase is a salt-active DNase.

3. The method according to claim 1, further comprising adding a Mg salt and/or a Mn salt to the biological sample, wherein the addition of said Mg salt and/or said Mn salt is sufficient to ensure a final concentration of Mg salt and/or Mn salt in the reaction mix of at least 1.0 mM.

4. The method according to claim 1, wherein the saponin comprises a monodesmosidic saponin.

5. The method according to claim 1, wherein the saponin comprises sapogenin.

6. The method according to claim 1, further comprising a subsequent step of extracting remaining nucleic acid after incubating the reaction mix.

7. The method according to claim 6, further comprising:
   (i) subjecting the extracted remaining nucleic acid to a purification process; and/or
   (ii) amplifying the extracted remaining nucleic acid; and/or
   (iii) conducting a nucleic acid amplification test on the extracted remaining nucleic acid or conducting a sequencing process on the extracted remaining nucleic acid.

8. The method according to claim 1, wherein the biological sample is a sputum sample or a blood sample.

9. The method according to claim 1, wherein the method that results in at least a 10 fold depletion of animal host DNA originally contained within the biological sample.

10. The method according to claim 1, wherein the addition of said NaCl and/or KCl is sufficient to ensure a final concentration of NaCl and/or KCl in the reaction mix of at least 1.0M.

11. The method according to claim 2, wherein the DNase is a DNase having the sequence of SEQ ID NO: 1 or of SEQ ID NO: 2.

12. The method according to claim 5, wherein the saponin comprises a triterpenoid.

13. The method according to claim 9, wherein the method results in at least a $10^2$-fold depletion of animal host DNA originally contained within the biological sample.

* * * * *